United States Patent
Wettergren et al.

(10) Patent No.: US 10,487,364 B2
(45) Date of Patent: Nov. 26, 2019

(54) ADMINISTRATION REGIME

(71) Applicant: ISOFOL MEDICAL AB, Gothenburg (SE)

(72) Inventors: Yvonne Wettergren, Gothenburg (SE); Elisabeth Odin, Gothenburg (SE)

(73) Assignee: ISOFOL MEDICAL AB (SE)

( * ) Notice: Subject to any disclaimer, the term of this patent is extended or adjusted under 35 U.S.C. 154(b) by 277 days.

(21) Appl. No.: 15/114,690

(22) PCT Filed: Jan. 30, 2015

(86) PCT No.: PCT/EP2015/051947
§ 371 (c)(1),
(2) Date: Jul. 27, 2016

(87) PCT Pub. No.: WO2015/114099
PCT Pub. Date: Aug. 6, 2015

(65) Prior Publication Data
US 2016/0340739 A1 Nov. 24, 2016

(30) Foreign Application Priority Data
Jan. 31, 2014 (EP) .................................... 14153538

(51) Int. Cl.
*C12Q 1/6886* (2018.01)
*G01N 33/574* (2006.01)
*A61K 31/519* (2006.01)

(52) U.S. Cl.
CPC .......... *C12Q 1/6886* (2013.01); *A61K 31/519* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2007/0099209 A1* 5/2007 Clarke .................. C12Q 1/6886 435/6.12
2009/0258795 A1* 10/2009 Cowens ............... C12Q 1/6886 506/16
2014/0087362 A1* 3/2014 Szalay ................... C07K 14/00 435/5

FOREIGN PATENT DOCUMENTS

EP 2617422 A1 7/2013
WO WO-2008115419 A2 9/2008

OTHER PUBLICATIONS

Odin, Elizabeth, et al:, "Altered gene expression of folate enzymes in adjacent mucosa is associated with outcome of colorectal cancer patients", Clinical Cancer Research: an official journal of the American Association for Cancer Research, Dec. 1, 2003 (Dec. 1, 2003), p. 6012, XP055121658, United States, Retrieved from the Internet: URL:<http://clincancerres.aacrjournals.org/content/9/16/6012.abstract>.

Sadahiro, Sotaro, et al: "Molecular determinants of folate levels after leucovorin administration in colorectal cancer", Cancer Chemotherapy and Pharmacology, Springer, Berlin, DE, vol. 65, No. 4, Jul. 28, 2009 (Jul. 28, 2009), pp. 735-742, XP019779234, ISSN: 1432-0843.

"Affymetrix Human Genome U133 Plus 2.0 Array [CDF: HGU133Plus2_Hs_ENSG v12.1.0]", GEO, Apr. 19, 2010 (Apr. 19, 2010), XP002668741, Retrieved from the Internet: URL: http://www.ncbi.nlm.gov/geo/quera/acc.cgi?acc=GPL9987 [retrieved on Apr. 19, 2010].

Bustin, S. A., et al: "The MIQE Guidelines: Minimum Information for Publication of Quantitative Real-Time PCR Experiments", Clinical Chemistry, vol. 55, No. 4, Feb. 26, 2009 (Feb. 26, 2009), pp. 611-622, XP055096284, ISSN: 0009-9147, DOI: <http://dx.doi.org/10.1373/clinchem.2008.112797>.

* cited by examiner

*Primary Examiner* — Channing S Mahatan
(74) *Attorney, Agent, or Firm* — Covington & Burling LLP (57) ABSTRACT

A method for determining a folate substance administration regime is disclosed. The method comprises: quantifying, in a sample drawn from a patient, the expression level of at least one of the genes SLC46A1, SLC19A1, FPGS, ABCC3, MTHFD1 L, GGH, MTHFD1, MTFMT, and ATIC; and establishing whether the expression level is high or low. A high expression level of at least one of said genes determines that said folate substance administration regime involves the administration of [6R]-methylenetetrahydrofolate and/or a folate substance upstreams of [6R]-methylenetetrahydrofolate in the metabolic pathway. A low expression level of at least one of said genes determines that said folate substance administration regime involves the administration of [6R]-methylenetetrahydrofolate. Also disclosed is a kit for determining such a folate substance administration regime.

6 Claims, 1 Drawing Sheet

ADMINISTRATION REGIME

PRIORITY STATEMENT

This patent application is a U.S. national stage filing under 35 U.S.C. § 371 of International Application No. PCT/EP2015/051947 filed on 30 Jan. 2015, which claims priority to European Patent Application No. 14153538.5 filed on 31 Jan. 2014. The entire disclosures of each of the above recited applications are incorporated herein by reference.

FIELD OF THE INVENTION

The present invention relates to a method for determining a folate substance administration regime, especially as part of a cancer treatment.

BACKGROUND OF THE INVENTION

Folic acid and various kinds of folic acid derivatives are commonly used as parts of different cancer treatments.

For example, leucovorin (folinic acid, LV) or its levo-isomer, levoleucovorin, and also other reduced folates, are frequently used in combination with fluorouracil (5-FU) in order to increase the anti-tumoral effect in treatment of patients with colorectal cancer. 5-FU+LV (FLV) treatment may be used alone or in combination with oxaliplatin or irinotecan as adjuvant as well as palliative treatment of colorectal cancer. Leucovorin or levoleucovorin is also used in combination with methotrexate as a "rescue agent" in order to reduce side effects of the methotrexate.

[6R]-5,10-methylenetetrahydrofolate (6R-methylenetetrahydrofolate, [6R]-MTHF, Modufolin®) is an endogenous folate metabolite now being developed for direct administration to patients with the aim to increase the efficacy and decrease the side effects of chemotherapeutic agents used in the treatment of solid tumors. It has been suggested that the use of the endogenous folate [6R]-MTHF in cancer treatment is more favourable than the use of other folic acid derivatives, e.g. leucovorin, since [6R]-MTHF is the active agent resulting from folate metabolism. In particular, it has been suggested that the administration of e.g. leucovorin is less efficient than the administration of [6R]-MTHF, since many metabolic steps are required in order to achieve the active species, i.e. [6R]-MTHF, from leucovorin. In practice, it has been seen that some patients nevertheless benefit from the administration of leucovorin as a part of cancer treatment, while in other patients, the positive effects can hardly be seen at all. The same is true for e.g. folic acid and levoleucovorin.

To date, the mechanisms underlying a successful folate treatment as part of a cancer treatment have not been resolved. The routine treatments involving e.g. folic acid, levoleucovorin or leucovorin are therefore frequently used for all patients, although this means that these substances are sometimes administered to patients as part of a cancer treatment without giving rise to any positive effects. This is not satisfactory in terms of any risks associated with the administration of unnecessary, non-active substances to patients, and also not in terms of cost efficiency. Furthermore, it is not satisfactory that the positive synergistic effects of the folate treatment, e.g. the increased anti-tumoral effect, do not appear in some patients. Neither is it satisfactory that the mediation of toxicity is difficult to predict or expect with certainty. There is thus a need in the art for a more predictable use of folic acid and folic acid derivatives in cancer treatment.

SUMMARY OF THE INVENTION

The present invention relates to a method for determining a folate substance administration regime, said method comprising:

quantifying, in a sample drawn from a patient, the expression level of at least one of the genes SLC46A1, SLC19A1, FPGS, ABCC3, MTHFD1L, GGH, MTHFD1, MTFMT, and ATIC; and establishing whether said expression level is high or low, wherein a high expression level of at least one of said genes determines that said folate substance administration regime involves the administration of [6R]-methylenetetrahydrofolate and/or a folate substance upstreams of [6R]-methylenetetrahydrofolate in the metabolic pathway, and wherein a low expression level of at least one of said genes determines that said folate substance administration regime involves the administration of [6R]-methylenetetrahydrofolate.

In one embodiment of the present invention, the step of quantifying the expression level of at least one of said genes is performed by real-time quantitative PCR, and the quantified expression level for each of said genes is preferably expressed as the Ct value normalized to the mean of the Ct values for the endogenous house-keeping genes β-actin and GAPDH. This normalized Ct value is also referred to as the ΔCt value.

In one embodiment of the present invention, the step of establishing whether said expression level is high or low comprises comparing the expression level of at least one of said genes with a predetermined cutoff value. Suitable cutoff values have been experimentally established, and the optimal cutoff values for available data are as follows:

the predetermined cutoff value for SLC46A1 is 9.8;
the predetermined cutoff value for SLC19A1 is 7.8;
the predetermined cutoff value for FPGS is 5.5;
the predetermined cutoff value for ABCC3 is 6.6;
the predetermined cutoff value for MTHFD1L is 6.3;
the predetermined cutoff value for GGH is 6.2;
the predetermined cutoff value for MTHFD1 is 6.9;
the predetermined cutoff value for MTFMT is 7.2; and
the predetermined cutoff value for ATIC is 6.0;

Each predetermined cutoff value is expressed as the Ct value normalized to the mean of the Ct values for the endogenous house-keeping genes β-actin and GAPDH.

As will be explained further below, the mean of the Ct values for the endogenous house-keeping genes β-actin and GAPDH have been subtracted from the Ct values, so an increase in the normalized values represent a decrease in expression. Consequently, a high expression level is indicated by a quantified expression level below the respective predetermined cutoff value, whereas a low expression level is indicated by a quantified expression level above the respective predetermined cutoff value.

The folate substance upstreams of [6R]-methylenetetrahydrofolate in the metabolic pathway is suitably selected from the group consisting of folic acid (pteroyl-L-glutamic acid), mefolinate ([6R,S]-5-CH₃-tetrahydrofolate), Metafolin® ([6S]-5-CH$_3$-tetrahydrofolate), CoFactor® ([6R,S]-5-CH$_2$-tetrahydrofolate), leucovorin ([6R,S]-5-CHO-tetrahydrofolate), and/or levoleucovorin ([6S]-5-CHO-tetrahydrofolate). In a preferred embodiment of the invention, the folate substance upstreams of [6R]-methylenetetrahydrofolate is levoleucovorin or leucovorin. Furthermore, the folate substance administration regime is suitably part of a cancer treatment.

The present invention for the first time presents a way to provide a customized folate treatment, especially as part of cancer treatment. In particular, the present invention has solved the problem of how to predict which patients who will benefit from a folate treatment involving folic acid or folic acid derivatives, like leucovorin, and also which patients who are more suited to be administered [6R]-methylenetetrahydrofolate directly. These findings are remarkable, and will provide a much more efficient and predictable handling of folate supplementation in cancer treatment, both from a medical and an economic perspective.

The invention is based on the surprising insight that the expression level of certain genes has a direct effect on a patient's capability to metabolize folic acid and its derivatives into [6R]-methylenetetrahydrofolate. The identified genes belong to three different categories:
folate transport (SLC46A1, SLC19A1, and ABCC3),
folate polyglutamation (FPGS and GGH), and
folate metabolism (MTHFD1L, MTHFD1, MTFMT, and ATIC)

According to one embodiment, the method according to the invention involves quantifying the expression of at least one of the genes belonging to the folate transport group, i.e. SLC46A1, SLC19A1, and ABCC3.

According to another embodiment, the method according to the invention involves quantifying the expression of at least one of the genes belonging to the folate glutamation group, i.e. FPGS, and GGH.

According to a further embodiment, the method according to the invention involves quantifying the expression of at least one of the genes belonging to the folate metabolism group, i.e. MTHFD1L, MTHFD1, MTFMT, and ATIC.

According to a preferred embodiment the method according to the invention involves quantifying the expression of at least one gene from each group, i.e. at least one of the genes SLC46A1, SLC19A1, and ABCC3; at least one of the genes FPGS, and GGH; and at least one of the genes MTHFD1L, MTHFD1, MTFMT, and ATIC.

When the folate substance administration regime is used as part of a cancer treatment, the cancer may be selected from the group consisting of breast cancer, gastric cancer, gall bladder cancer, bile duct cancer, colon cancer, rectal cancer, liver cancer, pancreatic cancer, head and neck cancer, and mesotheolioma cancer. The cancer treatment may involve the administration of an anti-cancer agent selected from the group consisting of antifolates, anthracyclines, platinum derivatives, topoisomerase inhibitors, and antimetabolites, such as fluorouracil.

The sample to be analyzed according to the inventive method is suitably drawn from a tumor of said patient, preferably a solid tumor.

The present invention also relates to a kit for determining a folate substance administration regime, said kit comprising:
means for quantifying, in a sample drawn from a patient, an expression level of at least one of the genes SLC46A1, SLC19A1, FPGS, ABCC3, MTHFD1L, GGH, MTHFD1, MTFMT, and ATIC; and means for establishing whether said expression level is high or low,
wherein a high expression level of at least one of said genes determines that said folate substance administration regime involves the administration of [6R]-methylenetetrahydrofolate and/or a folate substance upstreams of [6R]-methylenetetrahydrofolate in the metabolic pathway, and
wherein a low expression level of at least one of said genes determines that said folate substance administration regime involves the administration of [6R]-methylenetetrahydrofolate.

Based on the same inventive concept, the present invention also relates to
a method for identifying a patient susceptible for a folate substance administration regime involving the administration of a folate substance upstreams of [6R]-methylenetetrahydrofolate in the metabolic pathway, as well as a corresponding kit.
a method for identifying a patient particularly suited for a folate substance administration regime involving the administration of [6R]-methylenetetrahydrofolate, as well as a corresponding kit.
a method for identifying a patient susceptible for a cancer treatment involving the administration of an anti-cancer agent (e.g. 5-FU) and a folate substance upstreams of [6R]-MTHF in the metabolic pathway (e.g. leucovorin), as well as a corresponding kit.
a method for identifying a patient who is not susceptible for a cancer treatment involving the administration of an anti-cancer agent (e.g. 5-FU) and a folate substance upstreams of [6R]-MTHF in the metabolic pathway (e.g. leucovorin), as well as a corresponding kit.
a method for identifying a patient particularly suited for a cancer treatment involving the administration of an anti-cancer agent (e.g. 5-FU) and [6R]-methylenetetrahydrofolate, as well as a corresponding kit.

The inventive concept of identifying specific patient groups being susceptible for specific folate substance treatments also provides for establishing new further medical uses of folate substances upstreams of [6R]-MTHF in the metabolic pathway, [6R]-MTHF, and anti-cancer agents. In particular, the present invention provides for
an anti-cancer agent and a folate substance upstreams of [6R]-methylenetetrahydrofolate in the metabolic pathway for use in the treatment of cancer in a patient showing a high expression level of at least one of the genes SLC46A1, SLC19A1, FPGS, ABCC3, MTHFD1L, GGH, MTHFD1, MTFMT, and ATIC.
an anti-cancer agent and [6R]-methylenetetrahydrofolate for use in the treatment of cancer in a patient showing a low expression level of at least one of the genes SLC46A1, SLC19A1, FPGS, ABCC3, MTHFD1L, GGH, MTHFD1, MTFMT, and ATIC.

Analogously, the present invention provides for:
a method for treatment of cancer in a patient showing a high expression level of at least one of the genes SLC46A1, SLC19A1, FPGS, ABCC3, MTHFD1L, GGH, MTHFD1, MTFMT, and ATIC, comprising the administration of a pharmaceutically active amount of an anti-cancer agent and a folate substance upstreams of [6R]-methylenetetrahydrofolate in the metabolic pathway, and
a method for treatment of cancer in a patient showing a low expression level of at least one of the genes SLC46A1, SLC19A1, FPGS, ABCC3, MTHFD1L, GGH, MTHFD1, MTFMT, and ATIC, comprising the administration of a pharmaceutically active amount of an anti-cancer agent and [6R]-methylenetetrahydrofolate.

DETAILED DESCRIPTION OF THE INVENTION

In the research work leading to the present invention, it was surprisingly found that high expression of certain folate-associated genes is associated with a better effect of leucovorin administrated as part of cancer treatment. In particular, in a retrospective study in patients with colorectal cancer, high expression of certain folate-associated genes in tumor tissue was shown to correlate with decreased risk of recurrent disease.

Thus, it has been established that a low response to leucovorin therapy is linked to a low expression of one or more of the identified folate-associated genes. Accordingly, the reason why some patients do not benefit from the administration of leucovorin as a part of cancer treatment is that they are not able to metabolize the leucovorin into the active folate [6R]-MTHF to a sufficient extent.

Patients showing a low expression of these genes therefore benefit from the administration of the directly active folate [6R]-MTHF, which does not require metabolic activation and is therefore independent of these folate-associated genes. The same concept applies for other folate substances upstreams of [6R]-MTHF in the metabolic cycle, since they also require metabolic activation to exert the desired effect. All embodiments of the present invention are based on this surprising insight. On a general level, the present invention for the first time provides for the possibility to establish which patients that would benefit from the treatment of e.g. folic acid or leucovorin, and also which patient that would not benefit from such a treatment. This involves a remarkable improvement of the use of leucovorin and other folate substances in cancer treatments, since based on these findings, tailor-made treatment regimes can be established in order to provide as efficient treatments as possible. In particular, patients that do not have the capability to metabolize leucovorin are suitably administered the active folate metabolite, [6R]-MTHF, directly.

The genes identified are SLC46A1; SLC19A1; FPGS; ABCC3; MTHFD1L; GGH; MTHFD1; MTFMT; and ATIC. All these genes belong to the state of the art, and their sequences are well-characterized. In accordance with the present invention, each of these genes are described by reference to their respective reference human mRNA sequence(s) as provided by NCBI (National Center for Biotechnology Information).

In the NCBI database, the sequences are provided on the following format: [NM_$X_n$.Y], wherein "NM" indicates an mRNA sequence; "$X_n$" indicates the accession number; and "Y" indicates the version number. The version numbers are continually updated, and in Table 1, the most recent version by the indicated date is provided.

The genes SLC46A1; SLC19A1; FPGS; ABCC3; MTHFD1L; GGH; MTHFD1; MTFMT; and ATIC to be quantified in accordance with the present invention are completely and unambiguously identified by the accession numbers and version numbers indicated in Table 1 below. However, it is to be understood that similar reference sequences may also have the ability to provide an accurate identification. In particular, other versions of the reference sequences as provided by NCBI also have the ability to provide an accurate identification.

TABLE 1

| Gene | Transcript variant | Reference human mRNA sequence(s) (NCBI Reference Sequence(s)) - Accession number | Base pairs | Version number as of 28 Jan. 2014 |
|---|---|---|---|---|
| SLC46A1 | 1 | NM_080669 | 6510 | 5 |
|  | 2 | NM_001242366 | 6426 | 2 |
| SLC19A1 | 1 | NM_194255 | 2873 | 2 |
|  | 2 | NM_001205206 | 1885 | 1 |
|  | 3 | NM_001205207 | 2622 | 1 |
| FPGS | 1 | NM_004957 | 2308 | 5 |
|  | 2 | NM_001018078 | 2327 | 2 |
|  | 3 | NM_001288803 | 2230 | 1 |
| ABCC3 | 1 | NM_003786 | 5183 | 3 |
|  | 2 | NM_001144070 | 1958 | 1 |
| MTHFD1L | 1 | NM_001242767 | 3490 | 1 |
|  | 2 | NM_015440 | 3487 | 4 |
|  | 3 | NM_001242768 | 3174 | 1 |
|  | 4 | NM_001242769 | 1072 | 1 |
| GGH |  | NM_003878 | 1505 | 2 |
| MTHFD1 |  | NM_005956 | 3466 | 3 |
| MTFMT |  | NM_139242 | 2763 | 3 |
| ATIC |  | NM_004044 | 2094 | 6 |

The detailed sequence information on each gene can be found on NCBI's web site, world wide web address: ncbi.nlm.nih.gov/refseq.

The reason why some of the genes are described by reference to more than one mRNA reference sequence is that there exist mRNA splice variants. "Splicing" is a process occurring during gene expression, which results in a single gene coding for multiple proteins. In this process, particular exons of a gene may be included within, or excluded from, the mRNA produced from that gene, i.e. the gene may give rise to several different mRNA splice variants.

Three of the identified genes are involved in folate transport (SLC46A1, SLC19A1, and ABCC3), two of the identified genes are involved in folate polyglutamation (FPGS and GGH) and four of the identified genes are involved in folate metabolism (MTHFD1L, MTHFD1, MTFMT, and ATIC).

The gene SLC46A1 may alternatively be referred to as G21, HCP1, or PCFT.

The gene SLC19A1 may alternatively be referred to as CHMD, FOLT, IFC1, REFC, or RFC1.

The gene FPGS may alternatively be referred to as RP11-228B15.1.

The gene ABCC3 may alternatively be referred to as ABC31, EST90757, MLP2, MOAT-D, MRP3, or cMOAT2.

The gene MTHFD1L may alternatively be referred to as FTHFSDC1, MTC1THFS, RPI-292B18.2, or dJ292B18.2.

The gene GGH may alternatively be referred to as GH.

The gene MTHFD1 may alternatively be referred to as MTHFC, or MTHFD.

The gene MTFMT may alternatively be referred to as COXPD15, or FMT1.

The gene ATIC may alternatively be referred to as AICAR, AICARFT, IMPCHASE, OK/SW-cl.86, or PURH.

In its broadest sense, the present invention relates to a method for determining a folate substance administration regime, where the administration regime is determined depending on the expression level of one or more of the genes SLC46A1, SLC19A1, FPGS, ABCC3, MTHFD1L, GGH, MTHFD1, MTFMT, and ATIC.

If at least one of the genes SLC46A1, SLC19A1, FPGS, ABCC3, MTHFD1L, GGH, MTHFD1, MTFMT, and ATIC, shows a high expression level, it can be determined that the patient has the ability to metabolize a substance upstreams of [6R]-MTHF in the metabolic pathway into [6R]-MTHF, and thus, the administration regime may involve the administration of e.g. leucovorin. Of course, this patient category also benefits from the administration of [6R]-MTHF.

On the contrary, if at least one of the genes SLC46A1, SLC19A1, FPGS, ABCC3, MTHFD1L, GGH, MTHFD1, MTFMT, and ATIC, shows a low expression level, it can be concluded that the patient lacks the ability to sufficiently metabolize a substance upstreams of [6R]-MTHF in the metabolic pathway into [6R]-MTHF, and thus, the patient is suited for an administration regime involving the administration of [6R]-MTHF directly.

By the expression "high expression level" is meant an expression level of one of said genes, which involves a statistically significant decreased risk of recurrent disease (colorectal cancer), measured as disease-free survival, in patients treated with 5-FU in combination with leucovorin.

By the expression "low expression level" is meant an expression level of one of said genes, which involves a statistically significant increased risk of recurrent disease (colorectal cancer), measured as disease-free survival, in patients treated with 5-FU in combination with leucovorin.

In the experimental part below, a detailed explanation on establishing a high and low expression level, respectively, is provided.

In order to determine whether a patient shows a high or a low expression of a certain gene, the expression of one or more genes of interest is suitably examined by quantification by real-time quantitative PCR, which is a well-established technique used in the field for analysing gene expression levels. The quantified expression level for each of said genes is preferably expressed as the Ct value normalized to the mean of the Ct values for the endogenous house-keeping genes ACTB (β-actin) and GAPDH. These genes belong to the state of the art, and their sequences are well-characterized.

In accordance with the present invention, each of these housekeeping genes are described by reference to their respective reference human mRNA sequence(s) as provided by NCBI (National Center for Biotechnology Information).

In the NCBI database, the sequences are provided on the following format: [NM_$X_n$.Y], wherein "NM" indicates an mRNA sequence; "$X_n$" indicates the accession number; and "Y" indicates the version number. The version numbers are continually updated, and in Table 2, the most recent version by the indicated date is provided.

The house-keeping genes ACTB (β-actin) and GAPDH to be quantified in accordance with the present invention are completely and unambiguously identified by the accession numbers and version numbers indicated in Table 2 below. However, it is to be understood that similar reference sequences may also have the ability to provide an accurate identification. In particular, other versions (i.e. reference sequences having the same accession numbers, but different version numbers) of the reference sequences as provided by NCBI also have the ability to provide an accurate identification.

TABLE 2

| Housekeeping gene | Transcript variant | Reference human mRNA sequence(s) (NCBI Reference Sequence(s)) - Accession number | Base pairs | Version number as of 28 Jan. 2014 |
|---|---|---|---|---|
| ACTB | | NM_001101 | 1852 | 3 |
| GAPDH | 1 | NM_002046 | 1421 | 5 |
| | 2 | NM_001256799 | 1455 | 2 |

The gene ACTB may alternatively be referred to as BRWS1, or PS1TP5BP1.

The gene GAPDH may alternatively be referred to as CDABP0047, G3PD, or GAPD.

In a real-time quantitative PCR assay a positive reaction is detected by accumulation of a fluorescent signal. The Ct, "cycle threshold", is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample).

Normalization to an endogenous control (often referred to as a housekeeping gene) allows correction of results that can otherwise be skewed by differing amounts of input nucleic acid template. Any gene shown to be expressed at the same level in all study samples can potentially be used as an endogenous control.

According to the present invention, the step of establishing whether an expression level is high or low suitably comprises comparing the expression level of a gene of interest with a predetermined cutoff value. Suitable cutoff values have been experimentally established, and are listed in Table 6 below.

As the mean of the Ct values for the endogenous housekeeping genes β-actin and GAPDH have been subtracted from the Ct values, an increase in the normalized values represent a decrease in expression. Consequently, a high expression level is indicated by a quantified expression level below the respective predetermined cutoff value, whereas a low expression level is indicated by a quantified expression level above the respective predetermined cutoff value.

Specific examples of assays that may be used for analyzing the expression of the genes according to the invention are exemplified in Tables 3 and 4 (see also Example 1 and Table 5 below ("Assay ID")). The assays are provided by "Life Technologies", and detailed information on each assay can be found on their website, world wide web address: lifetechnologies.com.

As evidenced in Tables 3 and 4, the reference human mRNA sequences included in the exemplified analyses do not always have the version numbers listed in Tables 1 and 2. The reason for this is that there the exemplified assays were developed at a point in time where a previous version of the reference sequence was the most recent version.

TABLE 3

| Gene | Assay ID | Reference human mRNA sequence(s) (NCBI Reference Sequence(s)) included in analysis | Base pairs |
|---|---|---|---|
| SLC46A1 | Hs00611081_m1 | NM_080669.5 | 6510 |
| SLC19A1 | Hs00953344_m1 | NM_194255.2 | 2873 |
| | | NM_001205206.1 | 1885 |
| | | NM_001205207.1 | 2622 |

TABLE 3-continued

| Gene | Assay ID | Reference human mRNA sequence(s) (NCBI Reference Sequence(s)) included in analysis | Base pairs |
|---|---|---|---|
| FPGS | Hs00191956_m1 | NM_004957.4 | 2487 |
| | | NM_001018078.1 | 2475 |
| ABCC3 | Hs00358656_m1 | NM_003786.3 | 5183 |
| | | NM_001144070.1 | 1958 |
| MTHFD1L | Hs00383616_m1 | NM_001242767.1 | 3490 |
| | | NM_015440.4 | 3487 |
| | | NM_001242768.1 | 3174 |
| GGH | Hs00914163_m1 | NM_003878.2 | 1505 |
| MTHFD1 | Hs00602830_m1 | NM_005956.3 | 3466 |
| MTFMT | Hs00373739_m1 | NM_139242.3 | 2763 |
| ATIC | Hs00269671_m1 | NM_004044.6 | 2094 |

TABLE 4

| Housekeeping gene | Assay ID | Reference human mRNA sequence(s) (NCBI Reference Sequence(s)) included in analysis | Base pairs |
|---|---|---|---|
| ACTB | Hs99999903_m1 | NM_001101.3 | 1852 |
| GAPDH | Hs99999905_m1 | NM_002046.4 | 1401 |

The gene expression is preferably analyzed in a tissue sample drawn from a tumor of a patient, typically by a biopsy.

In one embodiment of the invention, the sample is analyzed for the expression of one or more genes from one of the gene groups mentioned above (i.e. genes involved in folate transport, folate polyglutamation, and folate metabolism, respectively). In another embodiment the sample is analyzed for the expression of one or more genes from two of the groups. In a preferred embodiment, the sample is analyzed for the expression of one or more genes from all of the three respective groups. In another preferred embodiment, the sample is analyzed for the expression of all nine genes. In one embodiment, the sample is analyzed for the expression of SLC46A1 and/or SLC19A1.

Some alternative denotations of [6R]-methylenetetrahydrofolate are: Modufolin®, [6R]-5,10-methylenetetrahydrofolate, [6R]-methylene-THF, [6R]-5,10-methylene-THF, [6R]-MTHF, [6R]-5,10-MTHF, [6R]-5,10-CH$_2$-THF, [6R]-5,10-CH$_2$-tetrahydrofolate, [6R]-5,10-CH$_2$-H$_4$PteGlu$_n$, The IUPAC name of methylenetetrahydrofolate is: N-[4-(3-amino-1-oxo-1,4,5,6,6a,7-hexahydroimidazo[1,5-f]pteridin-8(9H)-yl)benzoyl]-L-glutamic acid.

By the expression "a folate substance upstreams of [6R]-MTHF in the metabolic pathway" is meant any folate substance that upon administration to a patent is metabolized in the body to [6R]-MTHF. Examples of such substances are folic acid (pteroyl-L-glutamic acid), mefolinate ([6R,S]-5-CH$_3$-tetrahydrofolate), Metafolin® ([6S]-5-CH$_3$-tetrahydrofolate), CoFactor® ([6R,S]-5-CH$_2$-tetrahydrofolate), leucovorin ([6R,S]-5-CHO-tetrahydrofolate), and levoleucovorin ([6S]-5-CHO-tetrahydrofolate).

The expression "metabolic pathway" is a recognized expression within biochemistry and relates to a series of chemical reactions in a cell, catalyzed by enzymes and connected by their intermediates, i.e. the reactants of one reaction are the products of the previous one. The expression "upstreams of" defines that the folate substance in question is involved in a chemical reaction which occurs at an earlier stage in the series of chemical reactions than the chemical reaction leading to [6R]-MTHF.

Although the invention refers to a general method for determining a folate substance administration regime, it is particularly suitable for determining a folate administration regime which is part of a cancer treatment.

The present invention may be used in connection to the treatment of several cancer forms, e.g. breast cancer, gastric cancer, gall bladder cancer, bile duct cancer, colon cancer, rectal cancer, liver cancer, pancreatic cancer, head and neck cancer, and mesotheolioma cancer.

The cancer treatment may involve the administration of various anti-cancer agents, like antifolates, anthracyclines, platinum derivatives, topoisomerase inhibitors, and antimetabolites. The anti-cancer agents may be used alone or in combination. Suitable administration regimes of anti-cancer agents are known to a person skilled in the art.

Examples of antifolates to be used in accordance with the present invention are pemetrexed (Alimta®), raltitrexed (Tomudex®), methotrexate, and pralatrexate, all of which are transported by RFC (Reduced Folate Carrier). Other antifolates of interest are tumor-targeted antifolates, e.g. non-benzoyl 6-substituted straight chain pyrrolo[2,3-d]pyrimidine antifolates, that are specific substrates for transporters other than RFC with limited expression and/or transport into normal tissues compared with tumors. Examples of anthracyclines to be used in accordance with the present invention are daunorubicin, doxorubicin, epirubicin, idarubicin, and valrubicin. Examples of platinum derivatives to be used in accordance with the invention are oxaliplatin, cisplatin, carboplatin, satraplanin, picoplatin, nedaplatin, and triplatin. Examples of topoisomerase inhibitors to be used in accordance with the invention are irinotecan, topotecan, and camptothecin. Examples of antimetabolites to be used in accordance with the invention are fluorouracil (5-FU), floxuridine, cytosine arabinoside, and 6-azauracil.

The present invention also relates to a kit for determining a folate administration regime as defined above. Such a kit comprises some kind of means for quantifying, in a sample drawn from a patient, the expression level of at least one of the genes SLC46A1, SLC19A1, FPGS, ABCC3, MTHFD1L, GGH, MTHFD1, MTFMT, and ATIC.

The means may comprise an assay for analyzing the expression of one or more genes from one of the gene groups mentioned above (i.e. genes involved in folate transport (SLC46A1, SLC19A1, and ABCC3), folate polyglutamation (FPGS and GGH), and folate metabolism (MTHFD1L, MTHFD1, MTFMT, and ATIC), respectively). In another embodiment the means comprises an assay for analyzing the expression of one or more genes from two of the groups. In a preferred embodiment, the means comprises an assay for analyzing the expression of one or more genes from all of the three respective groups. In another preferred embodiment, the means comprises an assay for analyzing the expression of each of the nine genes (SLC46A1, SLC19A1, ABCC3, FPGS, GGH, MTHFD1L, MTHFD1, MTFMT, and ATIC). In one embodiment, the means comprises an assay for analyzing the expression of SLC46A1 and/or SLC19A1.

Suitably, the kit also comprises a leaflet indicating that a high expression level of at least one of the genes SLC46A1, SLC19A1, FPGS, ABCC3, MTHFD1L, GGH, MTHFD1, MTFMT, and ATIC, determines that the patient from which the sample is drawn is suited for a folate substance administration regime involving the administration of [6R]-MTHF and/or a folate substance upstreams of [6R]-MTHF in the metabolic pathway, and further that a low expression level of at least one of said genes SLC46A1, SLC19A1, FPGS, ABCC3, MTHFD1L, GGH, MTHFD1, MTFMT, and ATIC, determines that the patient from which the sample is drawn is suited for a folate substance administration regime involving the administration of [6R]-MTHF.

Based on the same inventive concept, the invention also relates to a method for identifying a patient susceptible for a folate substance administration regime involving the administration of a folate substance upstreams of [6R]-MTHF in the metabolic pathway, as well as to a corresponding kit.

Based on the same inventive concept, the invention also relates to a method for identifying a patient particularly suited for a folate substance administration regime involving the administration of [6R]-MTHF, as well as to a corresponding kit.

The underlying inventive concept also provides for a method for identifying a patient susceptible for a cancer treatment involving the administration of an anti-cancer agent (e.g. 5-FU) and a folate substance upstreams of [6R]-MTHF in the metabolic pathway (e.g. leucovorin), as well as a corresponding kit.

The underlying inventive concept also provides for a method for identifying a patient who is not susceptible for a cancer treatment involving the administration of an anti-cancer agent (e.g. 5-FU) and a folate substance upstreams of [6R]-MTHF in the metabolic pathway (e.g. leucovorin), as well as a corresponding kit.

The underlying inventive concept also provides for a method for identifying a patient particularly suited for a cancer treatment involving the administration of an anti-cancer agent (e.g. 5-FU) and [6R]-methylenetetrahydrofolate, as well as a corresponding kit.

The inventive concept of identifying specific patient groups being susceptible for specific folate substance treatments also provides for establishing new further medical uses of folate substances upstreams of [6R]-MTHF in the metabolic pathway, [6R]-MTHF, and anti-cancer agents.

In particular, the present invention provides for an anti-cancer agent (e.g. 5-FU) and a folate substance upstreams of [6R]-MTHF in the metabolic pathway (e.g. leucovorin) for use in the treatment of cancer in a patient showing a high expression level of at least one of the genes SLC46A1, SLC19A1, FPGS, ABCC3, MTHFD1 L, GGH, MTHFD1, MTFMT, and ATIC. The present invention also provides for an anti-cancer agent (e.g. 5-FU) and [6R]-MTHF for use in the treatment of cancer in a patient showing a low expression level of at least one of the genes SLC46A1, SLC19A1, FPGS, ABCC3, MTHFD1L, GGH, MTHFD1, MTFMT, and ATIC.

The invention will now be further explained in the following examples. These examples are only intended to illustrate the invention and should in no way be considered to limit the scope of the invention.

EXAMPLES

Example 1

The aim of Example 1 was to identify genes in the folate pathway with possible impact on the metabolism of LV, given according to the Nordic bolus regime (Carlsson, et al.; Sequential 5-fluorouracil and leucovorin in patients with advanced symptomatic gastrointestinal cancer, Eur J Cancer 1990; 26:874-6). Relative expression of 22 genes putatively involved in transport, polyglutamation and metabolism of LV was determined and related to disease-free survival (DFS) of patients with stage III colorectal cancer, who were given adjuvant treatment with FLV or with 5-FU, LV and oxaliplatin (FLOX).

Patients and Methods

Patients

During the period 2001-2009, 542 patients with non-hereditary stage III colorectal cancer underwent surgery at the Sahlgrenska University Hospital/Ostra and received adjuvant FLV (n=383) or FLOX (n=159) treatment. Out of the 542 patients, 446 underwent elective surgery. To enable comparison of gene expression in matched tumor and mucosa samples, it was necessary to collect and snap-freeze biopsies at surgery. Biopsy samples were obtained from 290 patients, and of these 193 were available for the current study.

All tumors were classified according to the Tumor-Node-Metastasis (TNM) staging system (Compton C, et al.; American Joint Committee on Cancer Prognostic Factors Consensus Conference: Colorectal Working Group; Cancer 2000; 88:1739-57). Patients were followed for 3-5 years after surgical removal of the primary tumor. The ethics committee of the University of Gothenburg approved the study and informed consent was obtained from all patients.

Treatment

Patients received adjuvant treatment with FLV or FLOX. FLV treatment comprised intravenous bolus injections of 5-FU (500 mg/m$^2$), followed by LV (60 mg/m$^2$) 30-40 minutes later, once weekly or on Days 1 and 2 every other week, according to the Nordic FLV regime (Carlsson, et al.; Sequential 5-fluorouracil and leucovorin in patients with advanced symptomatic gastrointestinal cancer, Eur J Cancer 1990; 26:874-6). FLOX treatment comprised 5-FU (500 mg/m$^2$) and LV (60 mg/m$^2$) bolus on Days 1 and 2 every other week, plus an oxaliplatin infusion (85 mg/m$^2$) over 120 minutes on Day 1 every other week (Sorbye H, Dahl O; Nordic 5-fluorouracil/leucovorin bolus schedule combined with oxaliplatin (Nordic FLOX) as first-line treatment of metastatic colorectal cancer, Acta Oncol 2003; 42:827-31).

Selection of Genes

Based on recent scientific literature (Sadahiro S, et al., *Molecular determinants of folate levels after leucovorin administration in colorectal cancer*, Cancer Chemother Pharmacol 2010; 65:735-42), 22 target genes with putative impact on LV metabolism were chosen for analysis (Table 5). Seven of these genes are involved in folate transport (ABCC1, ABCC3, FOLR1, FOLR2, FOLR3, SLC19A1/RFC-1 and SLC46A1/PCFT), whereas the other 15 genes encode enzymes involved in folate polyglutamation (FPGS and GGH) or folate metabolism (ALDH1L1, ALDH1L2, AMT, ATIC, FTCD, GART, MTFMT, MTHFD1, MTHFD1L, MTHFD2, MTHFS, SHMT1 and SHMT2).

TABLE 5

Gene list

| Gene category | Gene symbol | Gene name | Assay ID |
|---|---|---|---|
| Folate transport | ABCC1 | ATP-binding cassette, sub-family C (CFTR/MRP), member 1 | Hs00219905_m1 |
| | ABCC3 | ATP-binding cassette, sub-family C (CFTR/MRP), member 3 | Hs00358656_m1 |
| | FOLR1 | Folate receptor 1 (adult) | Hs01124177_m1 |
| | FOLR2 | Folate receptor 2 (fetal) | Hs00265255_m1 |
| | FOLR3 | Folate receptor 3 (gamma) | Hs01549264_m1 |
| | SLC19A1 | Solute carrier family 19 (folate transporter), member 1 | Hs00953344_m1 |
| | SLC46A1 | Solute carrier family 46 (folate transporter), member 1 | Hs00611081_m1 |
| Folate metabolism | ALDH1L1 | Aldehyde dehydrogenase 1 family, member L1 | Hs00201836_m1 |
| | ALDH1L2 | Aldehyde dehydrogenase 1 family, member L2 | Hs00402876_m1 |
| | AMT | Aminomethyltransferase | Hs00166628_m1 |
| | ATIC | 5-Aminoimidazole-4-carboxamide ribonucleotide formyltransferase/IMP cyclohydrolase | Hs00269671_m1 |
| | FTCD | Formiminotransferase cyclodeaminase | HS00198409_m1 |
| | GART | Phosphoribosylglycinamide formyltransferase, phosphoribosylglycinamide synthetase, phosphoribosylaminoimidazole synthetase | Hs00531926_m1 |
| | MTFMT | Mitochondrial methionyl-tRNA formyltransferase | Hs00373739_m1 |
| | MTHFD1 | Methylenetetrahydrofolate dehydrogenase (NADP+ dependent) 1, methenyltetrahydrofolate cyclohydrolase, formyltetrahydrofolate synthetase | Hs00602830_m1 |
| | MTHFD1L | Methylenetetrahydrofolate dehydrogenase (NADP+ dependent) 1-like | Hs00383616_m1 |
| | MTHFD2 | Methylenetetrahydrofolate dehydrogenase (NADP+ dependent) 2, methenyltetrahydrofolate cyclohydrolase | Hs00741165_m1 |
| | MTHFS | 5,10-methenyltetrahydrofolate synthetase (5-formyltetrahydrofolate cyclo-ligase) | Hs00197574_m1 |
| | SHMT1 | Serine hydroxymethyltransferase 1 (soluble) | Hs00541038_m1 |
| | SHMT2 | Serine hydroxymethyltransferase 2 (mitochondrial) | Hs00193658_m1 |
| Folate polyglutamation | FPGS | Folylpolyglutamate synthase | Hs00191956_m1 |
| | GGH | Gamma-glutamyl hydrolase (conjugase, folylpolygammaglutamyl hydrolase) | Hs00914163_m1 |
| House-keeping | ACTB | Actin, beta | Hs99999903_m1 |
| | GAPDH | Glyceraldehyde-3-phosphate dehydrogenase | Hs99999905_m1 |

Preparation of RNA and cDNA

Tumor and matched macroscopically normal-appearing mucosa (obtained approximately 10 cm from the tumor) were snap-frozen in liquid nitrogen after removal and stored at −70° C. until used. Total RNA was isolated from 10-30 mg fresh-frozen tissue using the High Pure RNA Tissue Kit (#12033674001, Roche Diagnostics Scandinavia AB) according to the manufacturer's instructions. cDNA was synthesized using the High Capacity cDNA Reverse Transcription Kit (Applied Biosystems) and run on Gene Amp PCR System 9600 (Perkin Elmer). To optimize each run, the expression level of β-actin was determined in each sample. A second RNA extraction and cDNA synthesis were performed if the concentration was considered to be suboptimal.

Real-Time Quantitative PCR

The relative gene expression was quantified using TagMan® Low-Density Array (TLDA) cards (Applied Biosystems). Custom-designed TLDA cards containing 24 individual assays were ordered from Applied Biosystems at world wide web address: appliedbiosystems.com. Three samples and one calibrator (SK-N-AS) were loaded to each card according to the manufacturer's instructions; each reservoir contained 83 ng of RNA converted to cDNA in a total volume of 100 µl. Two test runs were performed before the actual analysis. Quantitative polymerase chain reactions (QPCRs) were set up in duplicates in 384-well plates using the Biomek FX pipetting robot (Beckman Coulter) and were carried out in 10 µl reactions with 1×TaqMan® Gene Expression Mastermix (Applied Biosystems), 1×gene-specific assay and 7.5 ng RNA converted into cDNA. Both TLDA cards and individual QPCR plates were run and analyzed by the ABI PRISM® 7900HT Sequence Detection System (SDS 2.2, Applied Biosystems) according to the manufacturer's protocol. Calculations were performed using the ΔΔCt relative quantification method. The thresholds and baselines were set manually in SDS and Ct values were extracted. All Ct values were normalized to the mean of the endogenous house-keeping genes β-actin and GAPDH for each sample.

Statistics

Statistical analysis was performed using the 'survival' package in the R statistical software (Therneau T; *A Package for Survival Analysis in S. R package version* 2.37-4, world wide web address: CRAN.R-project.org/package=survival; 2013). Cox proportional-hazards regression models were applied to the data to examine the relationship between expression levels of chosen genes and the different censor variables. To choose between the numerous clinical covariates, stepwise model selection by Akaike information criterion (AIC) was performed on Cox models excluding the expression values. AIC is a measure of relative goodness of fit and, as long as it improved the AIC-value, the covariate that gave the best AIC if removed was deleted. The selected covariates were then included in the final models.

Cox regression was performed individually for each gene, for each gene for expression values from mucosa and tumor separately, and for one censor variable at a time. Furthermore, the difference between the mucosa and tumor was investigated in a separate model for each gene. Each of these models was fitted both with and without the additional selected clinical covariates to examine their influence on the models. Additionally, each pair of genes (tumor and mucosa) was fitted together to a Cox model in the same fashion, to examine possible interactions.

Statistical values of $p \leq 05$ were judged to be significant. Permutations were used to correct p-values for multiple testing. Furthermore, using the "qvalue" package in the R statistical software, false discovery rate q-values were calculated (Dabney A and Storey J D with assistance from Warnes G R; qvalue: Q-value estimation for false discovery rate control; R package version 1.32.0). There was a linear correlation between the two house-keeping genes β-actin and GAPDH. The expression of the target genes was related to a mean value representing both of these genes in order to keep variance to the minimum. DFS was calculated from the date of surgery to the last follow-up, or to the date of recurrence or death. All subjects that were disease-free at five years were censored at five years.

Determination of Cutoff Values

The optimal cutoff values were derived for one gene at the time. For each gene all possible cutoff values where none of the two groups consisted of less than 25% of the total number of observations were tested. Each cutoff value was tested through a logrank test comparing survival distributions of the two groups, and the cutoff value resulting in the smallest p-value from the logrank test was selected.

Calculations are made on Ct values normalized to the mean of the endogenous house-keeping genes β-actin and GAPDH for each sample. The means of the house-keeping genes were subtracted from the Ct values, so an increase in the normalized values still represents a decrease in expression.

The resulting cutoff values are presented in Table 6.

TABLE 6

| Gene | CutOff (ΔCt) |
|---|---|
| ABCC3 | 6.6 |
| ATIC | 6.0 |
| FPGS | 5.5 |
| GGH | 6.2 |
| MTFMT | 7.2 |
| MTHFD1 | 6.9 |
| MTHFD1L | 6.3 |
| SLC19A1 | 7.8 |
| SLC46A1 | 9.8 |

Results

Patient and tumor characteristics are shown in Table 7. The median age of patients at surgery was 65 years (range 35-80) and 92 (48%) patients were female. All tumors were classified as TNM stage III.

TABLE 7

| Patients (n = 193) and tumor characteristics | |
|---|---|
| Gender, n (%) | |
| Female | 92 (48) |
| Male | 101 (52) |
| Age, median (range) | 65 (35-80) |
| Tumor location, n (%) | |
| Right-sided colon | 47 (24) |
| Left-sided colon | 56 (29) |
| Right- and left-sided colon | 2 (1) |
| Rectum | 88 (46) |
| Tumor differentiation, n (%) | |
| High/Moderate | 152 (79) |
| Low | 32 (16) |
| Unknown | 9 (5) |
| Assessed lymph nodes, median (range) | 18 (3-63) |
| Positive lymph nodes, median (range) | 2 (1-31) |
| Lymph node ratio, median (range) | 15 (1.6-86) |

The multivariate Cox regression analysis included the parameters gender, age, lymph node ratio, tumor differentiation grade and adjuvant therapy (FLV or FLOX). Due to very low expression values of the house-keeping genes, one patient was considered to be an outlier and was excluded from the Cox regression analysis.

When doing stepwise variable selection with AIC, the two variables that emerged and which were included in the model were lymph node ratio and adjuvant therapy. Both varied to some extent in the different models, with lymph node ratio constantly having values of $p<0.01$, while adjuvant therapy was significant (at the $p \leq 05$ level) in only 42% of the models, although it constantly had values of $p<0.1$.

During follow-up, 59 of the 193 (31%) patients relapsed. A similar recurrence rate was found in 92 of the 253 (36%) patients who underwent elective surgery but from whom biopsy samples were not available. This indicates that the selected patient group was representative of the total cohort of patients treated with adjuvant FLV or FLOX therapy in 2001-2009.

There was a significant correlation between low expression of the following genes in tumor tissue and a increased risk of recurrent disease, measured as DFS: SLC46A1/PCFT ($p<0.001$), ABCC3 ($p<0.01$), FPGS ($p<0.01$), SLC19A1/RFC-1 ($p<0.01$), ATIC ($p<0.05$), GGH ($p<0.05$), MTFMT ($p<0.05$), MTHFD1 ($p<0.05$) and MTHFD1L ($p<0.05$) (Table 8). After correction for multiple testing, SLC46A1/PCFT and SLC19A1/RFC-1 remained significant with p-values<0.05.

TABLE 8

| Gene | Hazard ratio[a] | P | Pc[b] | q[c] |
|---|---|---|---|---|
| SLC46A1/PCFT | 1.30 | 0.00089 | 0.021 | 0.012 |
| SLC19A1/RFC-1 | 1.39 | 0.0016 | 0.035 | 0.012 |
| FPGS | 1.45 | 0.0038 | 0.071 | 0.019 |
| ABCC3 | 1.24 | 0.0051 | 0.093 | 0.019 |
| MTHFD1L | 1.30 | 0.016 | 0.24 | 0.049 |
| GGH | 1.18 | 0.025 | 0.34 | 0.065 |
| MTHFD1 | 1.32 | 0.038 | 0.45 | 0.070 |
| MTFMT | 1.38 | 0.038 | 0.46 | 0.070 |
| ATIC | 1.43 | 0.041 | 0.48 | 0.070 |
| GART | 1.16 | 0.17 | 0.92 | 0.25 |
| ABCC1 | 1.17 | 0.18 | 0.93 | 0.25 |
| SHMT1 | 0.92 | 0.26 | 0.98 | 0.31 |
| ALDH1L2 | 1.11 | 0.26 | 0.98 | 0.31 |
| MTHFD2 | 0.92 | 0.38 | 1.0 | 0.42 |
| FTCD | 0.96 | 0.51 | 1.0 | 0.52 |
| SHMT2 | 1.06 | 0.64 | 1.0 | 0.60 |
| FOLR1 | 1.02 | 0.66 | 1.0 | 0.60 |
| FOLR2 | 1.02 | 0.72 | 1.0 | 0.60 |
| MTHFS | 0.95 | 0.74 | 1.0 | 0.60 |
| ALDH1L1 | 0.99 | 0.79 | 1.0 | 0.60 |
| AMT | 1.00 | 0.96 | 1.0 | 0.68 |
| FOLR3 | 1.00 | 0.97 | 1.0 | 0.68 |

[a]Hazard ratios are calculated from ΔCt values and correspond to a halving of the expression levels.
[b]p-values corrected for multiple testing with permutations.
[c]False discovery rate q-value.

Figure 1:
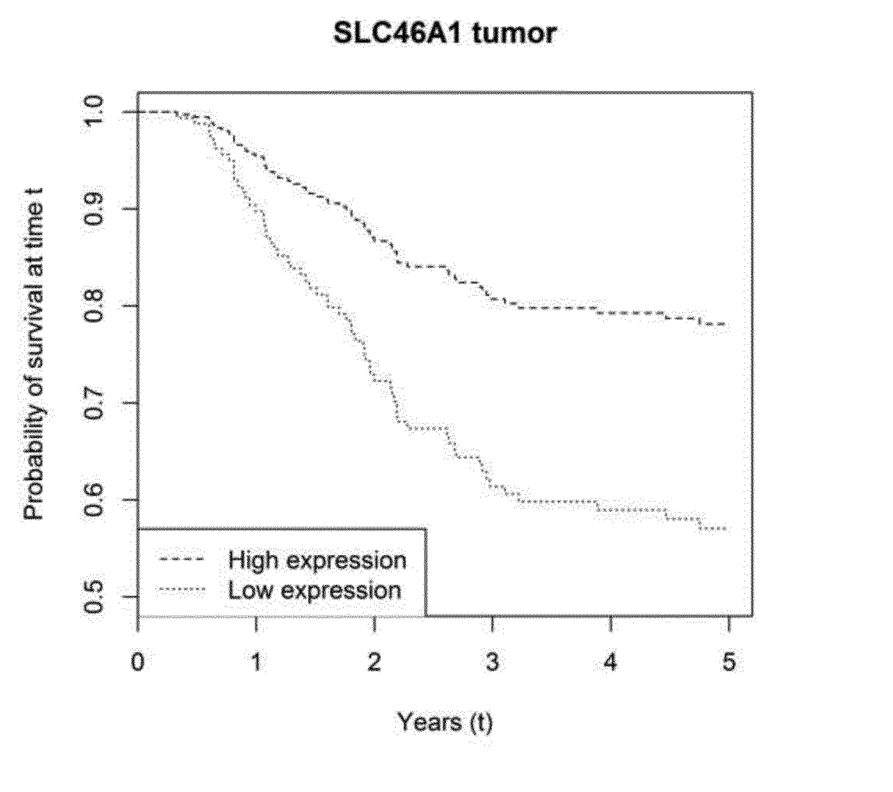
FIG. 1 shows estimated survival functions by level of SLC46A1 gene expression in colorectal cancer tumor.

Almost identical survival functions were obtained when the expression levels of the SLC46A1/PCFT, ABCC3, FPGS and SLC19A1/RFC-1 genes were plotted against time. A representative survival curve is shown in FIG. 1. FIG. 1 shows the estimated survival functions by level of SLC46A1/PCFT gene expression in colorectal cancer tissue. The two curves show predicted survival functions for the fitted Cox proportional hazards models. The expression levels for the two curves have been set one standard deviation above, and one standard deviation below the mean, where one standard deviation corresponds to a fold change in log expression levels of 1.57. Lymph node ratio has been set to its mean, and adjuvant therapy has been set to FLV since it was the treatment given to a majority of the patients. Standard deviations and mean for expression levels have been calculated from ΔCt values.

While the invention has been described in detail and with reference to specific embodiments thereof, it will be apparent for one skilled in the art that various changes and modifications can be made therein without departing from the spirit and scope thereof.

The invention claimed is:

1. A method for treating cancer in a patient comprising the step of administering a pharmaceutically active amount of an anti-cancer agent and [6R]-methylenetetrahydrofolate to said patient, wherein said method for treating a cancer patient is based upon a determination that said patient has a low expression level as compared with a cutoff value of at least one of the following genes:
   solute carrier family 46 (folate transporter), member 1 (SLC46A1);
   solute carrier family 19 (folate transporter), member 1 (SLC19A1);
   folylpolyglutamate synthase (FPGS);
   ATP-binding cassette, sub-family C (CFTC/MRP), member 1 (ABCC3);
   serine hydroxymethyltransferase 1 (soluble) (SHMT1);
   methylenetetrahydrofolate dehydrogenase (NADP+ dependent) 1-like (MTHFD1L);
   gamma-glutamyl hydrolase (conjugase, folylpolygamma-glutamyl hydrolase) (GGH);
   methylenetetrahydrofolate dehydrogenase (NADP+ dependent) 1, methenyltetrahydrofolate cyclohydrolase, formyltetrahydrofolate synthetase (MTHFD1);
   mitochondrial methionyl-tRNA formyltransferase (MTFMT); and
   5-aminoimidazole-4-carboxamide ribonucleotide formyltransferase/IMP cyclohydrolase (ATIC);
   wherein the cutoff value is expressed as a cycle threshold (Ct) value normalized to a mean Ct value for endogenous house-keeping genes β-actin and glyceraldehyde-4-phosphate dehydrogenase (GAPDH),
   wherein a low expression level is indicated by a Ct value above the cutoff value.

2. The method of claim 1, wherein the expression level of at least one of said genes is determined by real-time quantitative PCR.

3. The method of claim 1, wherein:
   the cutoff value for SLC46A1 is 9.8;
   the cutoff value for SLC19A1 is 7.8;
   the cutoff value for FPGS is 5.5;
   the cutoff value for ABCC3 is 6.6;
   the cutoff value for MTHFD1 L is 6.3;
   the cutoff value for GGH is 6.2;
   the cutoff value for MTHFD1 is 6.9;
   the cutoff value for MTFMT is 7.2;
   the cutoff value for ATIC is 6.0.

4. A method for treating cancer in a patient comprising the step of administering a pharmaceutically active amount of an anti-cancer agent and a folate selected from the group consisting of folic acid, [6R,S]-5-CH$_3$-tetrahydrofolate, [6S]-5-CH$_3$-tetrahydrofolate, [6R,S]-5-CH$_2$-tetrahydrofolate, [6S]-5-CHO-tetrahydrofolate, and [6R,S]-5-CHO-tetrahydrofolate to said patient, wherein said method for treating a cancer patient is based upon a determination that said patient has a high expression level as compared with a cutoff value of at least one of the following genes: selected from the group consisting of SLC46A1, SLC19A1, FPGS, ABCC3, SHMT1, MTHFD1L, GGH, MTHFD1, MTFMT, and ATIC,
   wherein the cutoff value is expressed as a Ct value normalized to a mean Ct value for endogenous house-keeping genes β-actin and GAPDH,
   wherein a high expression level is indicated by a Ct value below the cutoff value.

5. The method of claim 4, wherein the expression level of at least one of said genes is determined by real-time quantitative PCR.

6. The method of claim 4, wherein:
   the cutoff value for SLC46A1 is 9.8;
   the cutoff value for SLC19A1 is 7.8;
   the cutoff value for FPGS is 5.5;
   the cutoff value for ABCC3 is 6.6;
   the cutoff value for MTHFD1L is 6.3;
   the cutoff value for GGH is 6.2;
   the cutoff value for MTHFD1 is 6.9;
   the cutoff value for MTFMT is 7.2;
   the cutoff value for ATIC is 6.0.

* * * * *

UNITED STATES PATENT AND TRADEMARK OFFICE
CERTIFICATE OF CORRECTION

PATENT NO. : 10,487,364 B2
APPLICATION NO. : 15/114690
DATED : November 26, 2019
INVENTOR(S) : Wettergren et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 321 days.

Signed and Sealed this
Eighth Day of December, 2020

Andrei Iancu
*Director of the United States Patent and Trademark Office*